United States Patent [19]

Costin

[11] Patent Number: 5,733,256

[45] Date of Patent: Mar. 31, 1998

[54] INTEGRATED PHACOEMULSIFICATION SYSTEM

[75] Inventor: John A. Costin, Vermilion, Ohio

[73] Assignee: Micro Medical Devices, Wakeman, Ohio

[21] Appl. No.: 721,331

[22] Filed: Sep. 26, 1996

[51] Int. Cl.$^6$ ................................................ A61B 17/20
[52] U.S. Cl. ........................... 604/22; 604/27; 604/28; 604/30; 604/31; 604/35; 604/43; 606/107
[58] Field of Search ........................ 604/22, 27, 28, 604/30, 31, 35, 43; 606/107

[56] References Cited

U.S. PATENT DOCUMENTS

| | | | |
|---|---|---|---|
| 5,151,085 | 9/1992 | Sakurai et al. | 604/22 |
| 5,406,503 | 4/1995 | Williams, Jr. et al. | 604/22 |
| 5,419,761 | 5/1995 | Narayanan et al. | 604/22 |

*Primary Examiner*—Michael Buiz
*Assistant Examiner*—Daphja Shaz
*Attorney, Agent, or Firm*—Fish & Richardson P.C.

[57] ABSTRACT

Surgical system for phacoemulsification providing infusion fluid apparatus and aspiration or evacuation apparatus to supplement the action of ultrasound vibrational energy applied to the surgical target area via a surgical handpiece. The supplemental apparatus for infusion and aspiration maintains a stable control volume within the anterior chamber of the human eye during a phacoemulsification procedure. Integration of the fluid pressure and flow sensors in a close proximity of less than 8 inches with the surgical handpieceand reduction of communicating fluid pressure and flow rate via fluid conduits allows fast system response time and accurate operation control.

9 Claims, 12 Drawing Sheets

INTEGRATED PHACOEMULSIFICATION SYSTEM

FIELD OF INVENTION

The present invention relates to a surgical control system. More particularly, the present invention relates to a surgical control system for phacoemulsification in which various parameters are sensed at a location that is close to the point of operation.

BACKGROUND AND SUMMARY

Phacoemulsification is a process used during cataract surgery. Cataract surgery uses ultrasonic vibration to liquefy parts of an affected lens. The emulsified cataract tissue is then removed by a specialized form of suction.

This cataract removal methodology has several documented advantages over other earlier methods of cataract extraction. An important advantage includes the reduction of incision size, and trauma associated with the extraction process. Also of great benefit is the continuous improvement of control methods to give the surgeon simultaneous control over ultrasound energy, infusion fluid flow and pressure, and aspiration fluid flow and vacuum, all of which affect the stability of tissue structures at the surgical site within anterior chamber the human eye.

U.S. Pat. No. 5,279,547, listing the present inventor, describes a special control system for such suction operation. The system described in this patent avoids many of the problems that have been associated with punching through the eye from the force of the suction.

Traditional phacoemulsification has evolved dramatically since the introduction of the early systems like the Kellman Cavitron, particularly over the last five or ten years. Many variations of control methodology have been applied to the extraction of cataracts using electronically driven ultrasonic transducers housed in hand-held enclosures that integrate aspiration and infusion fluid conduits. These integrated handpieces, in conjunction with various actuator and sensor mechanisms housed within the confines of the control system console, provide a surgeon with a single hand-held tool that allows performing nearly the entire phacoemulsification process.

The principal elements of systems used in this procedure include the ultrasound transducer, the actuator, feedback, and control electronics, the apparatus for generating vacuum, and the mechanism for delivering infusion fluid. integrated systems employ microprocessor, actuator, and sensor technology to manipulate the parameters of ultrasound power, fluid flow and pressure. Both the aspiration and infusion fluid channels are connected directly to the ultrasound transducer housing.

One important goal of successful phacoemulsification surgery is to extract the cataract while minimizing the trauma to neighboring tissue. The inventor of the present invention determined that an optimum environment to achieve this goal would include systems employing instruments and control methodologies that minimize fluctuations in intraocular pressure during the procedure.

Positive intraocular pressure is maintained by the balance between flow of infusion fluid at positive pressure and the evacuating flow of fluid with emulsified cataract tissue. The fluid flow is pulled through the aspiration channel as a result of a vacuum level operating at some distance from the handpiece tip.

In this system, the surgeon plays the role of the primary sensor and controller in a classical "Person in the Loop" control system. The surgeon observes the stability of the fluid volume in the anterior chamber of the human eye and attempts to adjust the fluid balance by communicating desired changes in ultrasound power, aspiration, vacuum level, and infusion fluid pressure back to the system controller, through various means. A foot controller, similar in function to the accelerator pedal controlling the speed of an automobile, is often used to control fluid pressure, for example.

The surgeon's actions are supplemented by the microprocessors that control various actuators based on the information communicated by the surgeon (primary feedback sensor) and by secondary feedback sensors. These sensors are located within the boundary of the system console. They measure ultrasonic power, vacuum, and fluid flow. In some cases, these measurements are indirect because of the nature of the parameter under scrutiny.

Two common indirect measurements include the amount of ultrasonic power at the transducer tip and an amount of fluid flow through the aspiration channel. The ultrasonic power at the transducer tip is commonly sensed from the amount of electrical power consumed at the input terminals of the handpiece connector, located at the system console. Characterization of the transducer ultrasound output as it correlates with electrical power consumption, allows the microprocessor to be preprogrammed with the mapping of that correlation.

Fluid flow is often sensed from the correlation between the combination of vacuum levels at the console and the physical dimensions of the aspiration fluid conduit, including all of the flexible tubing connecting the system console collection cassette and the surgical handpiece. Similarly, with peristaltic pump systems, an inference is made between the combination of pump motor speed and the physical dimensions of the flexible tubing engaged by the pump rollers.

One critical element necessary for the application of optimum intraocular pressure control is the physical location of the responsive feedback sensors relative to the region where parameters of fluid flow and pressure are to be controlled. In the case of phacoemulsification, the region of interest is the anterior chamber of the human eye.

The inventor of the present invention recognized significant limitations in the prior art. One such limitation results from the sensors being deployed at a significant distance from the tip of the ultrasound transducer. Beyond the inherent limitations of controlling parameters based on indirect measurements, excessive physical distance between the sensor and the point of energy application may exacerbate certain errors. The dynamic fluid flow and pressure characteristics of the fluid volume in the anterior chamber of the human eye also become difficult to observe and control. The volume of the anterior chamber is small and therefore small changes in volume can translate to large changes in the physical environment.

An argument could be made that direct control is virtually impossible in this situation. The distances between the sensors and the point where pressure and fluid dynamics are to be controlled are typically in excess of 6 feet. In electronic terms, that distance is infinitesimal since the electrical field propagates on the same order as the speed of light. In fluid terms, where the information is transmitted by a compressible fluid in a very compliant channel of varying dimension, possibly with some volume of gas and emulsified tissue interrupting the continuous fluid transmission, that distance is enormous. This distance translates to a long delay time for the fluid motion. This delay time can prove to be a problem.

This situation is in contrast to high pressure hydraulic systems where the fluid is uncontaminated and conduit for fluid transmission is rigid. The known physical dimensions and tight tolerances greatly improves the possibility of extracting accurate information from the fluid stream.

The limitations caused by this problem are documented. For example, in U.S. Pat. No. 4,019,514 to Banko describes the inherent limitations of this patented apparatus relative to the location of sensors necessary to engage the responsive control means. See for example clause 11, which states "Since it is not practical to have a pressure sensor in the eye it is impossible to define and keep track of its internal pressure at any and every instance during the operation."

Prior art systems that attempt to control fluid flow and pressure variations in the anterior chamber rely on inherent characteristics of the vacuum or fluid flow generating mechanism to infer the parameter variation at the ultrasound tip. These systems employ closed loop feedback from the flow and pressure sensors which input parameter variation to a microprocessor. Control software applies various control algorithms and injects changes via actuators into the fluid flow or vacuum generator such that the principal energy delivery characteristic is altered.

For example, in patented venturi closed loop aspiration control system by Alcon Laboratories, the air flow to the venturi is modified such that the vacuum generated at its output matches the value commanded by the operator. In this case, the principal energy delivery characteristic is at vacuum level (or negative pressure). The sensor for the feedback loop is located in close proximity to the rigid cassette at the system console. The cassette is connected to the ultrasound handpiece by a length of at least 6 feet of flexible tubing. Therefore, the closed loop control follows the vacuum level at the console, not that at the anterior chamber of the human eye.

In peristaltic pump systems, the principal energy delivery characteristic is fluid flow which can be inferred from the speed of the motor that drives the pump. In this case, a microprocessor alters the motor speed to achieve the desired fluid flow commanded by the user. Pressure or vacuum can also be measured by various sensor technologies. But again, the feedback loop is closed at the system console, not at the point of energy application in the anterior chamber, which is typically over 6 feet away.

Other related U.S. patents held by Banko, assigned to Surgical Design Corporation, include the following, all dated between 1974 and 1978: U.S. Pat Nos. 3,812,855; 3,920,014; 4,007,742; and 4,117,843. These patents relate to apparatus for controlling the combination of infusion fluid and aspiration fluid flow and pressure for the purpose of stabilizing the control volume of the operating field, included in such stabilization is the provision for managing various flows and pressures under adverse conditions such as unplanned occlusion in the aspiration channel or the necessary switching between surgical operating modes, each of which may require a different combination of infusion and aspiration parameters.

Some prior art addresses the issues of fluid flow and eye pressure by proposed modifications to the infusion and aspiration channels in close proximity with the surgical handpiece tip. U.S. Pat. No. 3,805,787 to Banko describes an apparatus that comprises a combination of rigid metallic sleeves for the ultrasound handpiece tip to provide irrigation and aspiration while shielding the surrounding tissue in the anterior chamber from undesirable vibration fields transverse to the longitudinal axis of the tip.

Prior art also includes various modifications to the ultrasound transducer tips to enhance the efficiency of ultrasound vibrational energy transmitted to the cataract. Some of these modifications simultaneously modify the fluid flow and pressure response characteristics of the fluid volume in the anterior chamber of the human eye. For example, the Zellman Small-Port-Phaco™ Tip was designed primarily to improve the efficiency of ultrasound vibration transmission by increasing the tip surface area in the plane normal to the transmission path. The size of the aspiration opening was decreased as a result of increasing the tip surface area, while holding the tip outside diameter constant. This decreased orifice size had the effect of reducing the fluid flow from the anterior chamber into the aspiration channel beginning at the tip.

Some modifications to the ultrasound tip in the prior art are specifically designed to modify the fluid flow and pressure characteristics of the fluid volume in the anterior chamber. The Mackool Microseal™ system added a rigid insert between the outside diameter of the ultrasound tip and the inside diameter of the flexible irrigation sleeve. The irrigation sleeve is used to channel infusion fluid from the ultrasound handpiece infusion conduit into the anterior chamber.

A tradeoff exists between the incision size of the entry wound, and the amount of fluid leakage experienced around the tip that is inserted through the wound. As surgeons reduce the incision size from 3.5 mm to 3.2 mm to 2.7 mm to minimize the wound leakage, certain ultrasound tips would behave in a fashion such that friction between the irrigation sleeve and the titanium metal tip would generate heat. The heat is transmitted to the tissue in contact with the irrigation sleeve at the entry wound. In some cases, heat transmission is sufficient to alter the characteristics of the tissue and its appearance.

U.S. Pat. No. 5,342,293 to Zanger captures the essence of the phacoemulsification fluid flow and pressure issues. The fundamental concept is that, integrated control of fluid flow and pressure for both infusion and aspiration is necessary to ensure stability of the anterior chamber volume during cataract removal. Without this stability, the risk to other tissue entities is increased. e.g., the iris and cornea endothelial layer.

Other systemic configuration device patents describe other ways to draw the inference between parameters measured at some distance from the operating site, and the actual fluid dynamics within the anterior chamber of the human eye.

In a similar vein, the SMART PHACO system apparatus that is patented by John Costin takes advantage of sophisticated electronic sensing and digital signal processing methods to infer the tissue characteristics at the ultrasound tip. By means of mapping the known, experimental, electrical power consumption characteristics of the ultrasound transducer and comparing those known characteristics with those observed in real time during phacoemulsification surgery, adjustments are implemented for all three primary surgical parameters: ultrasound power, infusion, and aspiration. The adjustments achieve optimum emulsification of the cataract, minimum risk to surrounding tissues, and reduced likelihood of occlusions in the aspiration channel. Subsequently, this allows minimization of unwanted pressure fluctuations within the anterior chamber by minimizing the likelihood of interruption of evacuation fluid flow through the aspiration channel.

In view of the above, the present invention defines a system that allows direct measurement and control of fluid dynamics within the anterior chamber of the human eye during phacoemulsification surgery.

To summarize, the control methodology of the prior art receives only indirect information inferred from sensors located at some significant distance from the anterior chamber of the human eye. Additional limitations in the prior art are induced by fluid flow and pressure information loss due to transmission through compliant channels. Further complicating this problem is an inherent nature of the operation target-the very small volume of the anterior chamber.

FIG. 1 shows the typical configuration of a surgical system of the prior art used in phacoemulsification. A system console 100 is the controlling center, housing all actuators, sensors, and control electronics.

The integrated phacoemulsification handpiece 110 houses a ultrasonic acoustic transducer to convert the electrical energy input to vibrational energy output for application to the acoustic load at the surgical site 120. The handpiece 110 also provides rigid conduits for irrigation and aspiration fluid. The coupling between the system console 100 and the phacoemulsification handpiece 110 is compliant, flexible conduit which is typically in the form of PVC or silicon tubing. The diagram in FIG. 1 also shows the conduits 132, 134, 136, which each span a relatively long distance separating the system console 100 from the phacoemulsification handpiece 110.

FIG. 2 shows additional detail of the prior art system as in FIG. 1, emphasizing the interconnection between the drive circuits (actuators) and the fluid streams for infusion and aspiration. FIG. 2 also shows the interconnection between sensors 104 and 106 that are housed within the console 100 and the feedback circuits which operate on the analog electronic signals generated by the sensors. The system microprocessor 102 receives information in the appropriate digital format at the output of the data conversion block (Analog to Digital or A/D) 200. The system microprocessor 102 then operates on the feedback information, applies appropriate software control algorithms, and generates correction signals. The digital correction signals move through data conversion block (Digital to Analog D/A) 202, and then to system drive circuits (actuators).

FIG. 3 is similar to FIG. 1, but shows even more detail about the sensor blocks of the prior art. Again, the sensors for pressure, vacuum, and flow are physically located within the confines of the system console 100. As shown in FIG. 3, separate sensors are used for flow and pressure (or vacuum) for irrigation and aspiration. The measurement of flow in the prior art is usually an inferred measurement rather than a direct measurement. Typically, in a peristaltic pump system, flow is inferred from measurements of pump motor speed. Pressure and vacuum measurement in prior art is typically performed by a strain gauge type device with a flexible diaphragm. These devices are physically large, typically in excess of one half inch on a side, which limits their usefulness when attempting to integrate the sensor into the surgical handpiece or a small ancillary module in close proximity with the surgical handpiece.

Once the sensors convert the physical parameter being measured to electrical signals, those electrical signals travel at nearly the speed of light, essentially appearing instantaneously at the data conversion block. The total delay, from the time the electrical signals appear at the data conversion block until the processed electrical signals are applied to the actuators, is measured in milliseconds. The major portion of the delay is due to the complexity of the software control algorithm that the microprocessor 102 must implement.

In some systems, a single microcontroller could be used to process the control for a single function. For example, all parameters related to fluidics could have a dedicated microcontroller. Another microcontroller could process all information relating to ultrasonic power. Possibly an additional microcontroller could be dedicated to user interface information from the console front panel. In those systems, the total delay to process information for a given function would be even less than that of systems that have a single central microprocessor to control all functions.

One major time delay in system response is critical to system performance. The major point to be emphasized is that time delay should be minimized between a parameter change event and the actuator output to adjust the parameter which has changed. In surgical control system applications, the available technology in electronics, microprocessors, and software implementation virtually eliminates time delays once information is converted into electrical signals. The remaining sources of time delay are due to traditional sensor technology, and the inherent response characteristics of physical systems being controlled. The other obvious source of delay, as described with the prior art, is the fluid flow and pressure information loss due to the length and compliance of the transmission signal path between the point where the parameter is to be controlled and the point where the parameter is measured by the sensor.

The time delay limitations associated with traditional sensor technology can be considered in two categories. First is the time required to convert physical parameters being measured into electrical signals. In terms of the surgical control system, sensor conversion delays are insignificant to the total delay.

Another limitation of traditional sensors is their physical size and resiliency when operating under extreme temperatures, such as high temperature steam in a sterilization process. These limitations of traditional sensors have restricted the choices for their physical location within the system. As emphasized in the prior art surgical system block diagrams FIGS. 1-3, the traditional sensors 104 and 106 for fluid flow, vacuum, and pressure have been confined to reside within the boundary of the system control console 100. The time delays associated with these physical limitations are significant to the control process.

In view of the reasons and limitations of the prior art described above, the inventor of the present invention has realized that certain improvements can operate in a way that improves the surgical systems for phacoemulsification with fast, precise and automatic control of ultrasound output energy, infusion fluid flow and pressure, and aspiration fluid flow and vacuum. The present invention is called by the inventors the "prefix" Pro-PHACO system. The present invention describes methods and devices to overcome many technological problems in existing surgical systems for phacoemulsification.

In particular, the present invention minimizes the distance between the point of application of principal characteristic energy, i.e., infusion fluid flow and pressure in combination, and aspiration fluid flow and pressure in combination, that is used in cataract extraction via phacoemulsification, and the feedback sensor. The sensor is electronically linked to the control mechanism. This greatly improves the speed and precision of the measurement and control of fluid flow and pressure parameters.

One of the novel features in the present invention is the integration of the sensors for pressure and fluid flow into the housing for the ultrasound transducer. This eliminates the long and imprecise fluid transmission path (typically 6 feet or more) which is a source of error for the feedback loop. In contrast, the prior art requires the actuator correction signal to be applied at the system console and the change in the principal characteristic source must be transmitted over a long path (e.g., approximately 6 foot) to the anterior chamber. Furthermore, the resulting response at the anterior chamber must be transmitted back to the system console over the same distance which adds an additional delay in the system feedback. The present invention dramatically reduces the delay between the actuator correction signals and the response at the anterior chamber of the human eye, possibly by as much as a factor of 2, and significantly minimizes control errors in the feedback loop.

There is an additional benefit of minimizing the distance between the sensor and the point where the fluid flow and pressure characteristics are to be measured due to the availability of predictive adaptive control software algorithms. These algorithms provide the capability of anticipating changes at macroscopic level in system dynamics from observations of changes at microscopic level. The concept of expert systems and artificial intelligence can be implemented into the present invention by allowing the microprocessor control to adapt its actuator control signals to learned variations in pressure and fluid flow for optimum system response.

Advantages of placing sensors in close proximity with the point of application of principal characteristic energy in the present invention also lie in the improved quality of the information transmitted from the surgical site to the control system. If the means of communication between the surgical site and the console control system is limited to the fluid stream between them, there is a large likelihood that much information relative to the pressure and flow conditions at the surgical site will have been lost. This is one of factors that limits the prior art in which the path between the console and the phacoemulsification handpiece is a flexible conduit. With this conduit extending a long distance (typically, 6 feet or more), rapid and subtle pressure fluctuations as well as high-speed microscopic flow streams at the surgical site will likely be washed out by the inherent low-pass-filter characteristics of the compliant signal transmission path (the flexible conduit).

The present invention achieves all of the foregoing objects and thereby constitutes a significant improvement over prior art. The advantages of the present invention will become more apparent in the light of the following detailed description of preferred embodiments thereof, as illustrated in the accompanying drawings.

DETAILED DESCRIPTION

The "prefix" PRO-PHACO System deploys fluid flow and pressure sensors in close proximity with the surgical target area, compared with the traditional sensor deployment within the confines of the surgical console.

A first embodiment uses sensors contained within a remote sensor module located very close to the surgical handpiece, at a distance of typically several inches from the handpiece fluid conduit interfaces. The second embodiment integrates the sensor module within the surgical handpiece.

Figure 4:
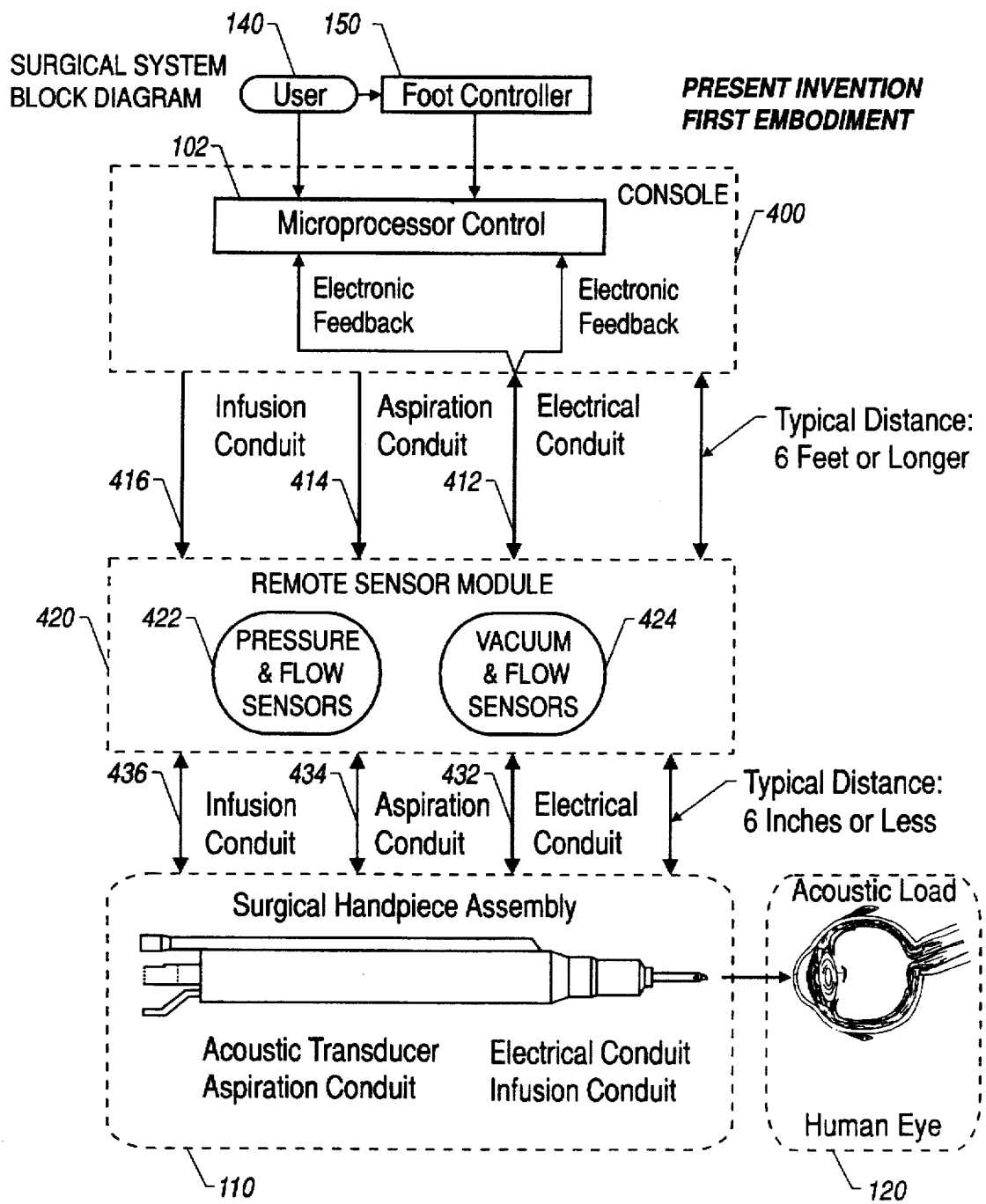
FIG. 4 is a block diagram of the first embodiment of the present invention.

A block diagram of the first embodiment of the present invention is shown in FIG. 4. A remote sensor module 420 is located between the surgical handpiece 110 and the control console 400. Remote sensor module 420 includes pressure/flow sensors 422 and vacuum/flow sensors 424. Electrical feedback signals are produced from these sensors 104 and 106 and are transmitted via the electrical conduit 412 at rapid electronic transmission speeds.

Figure 1:
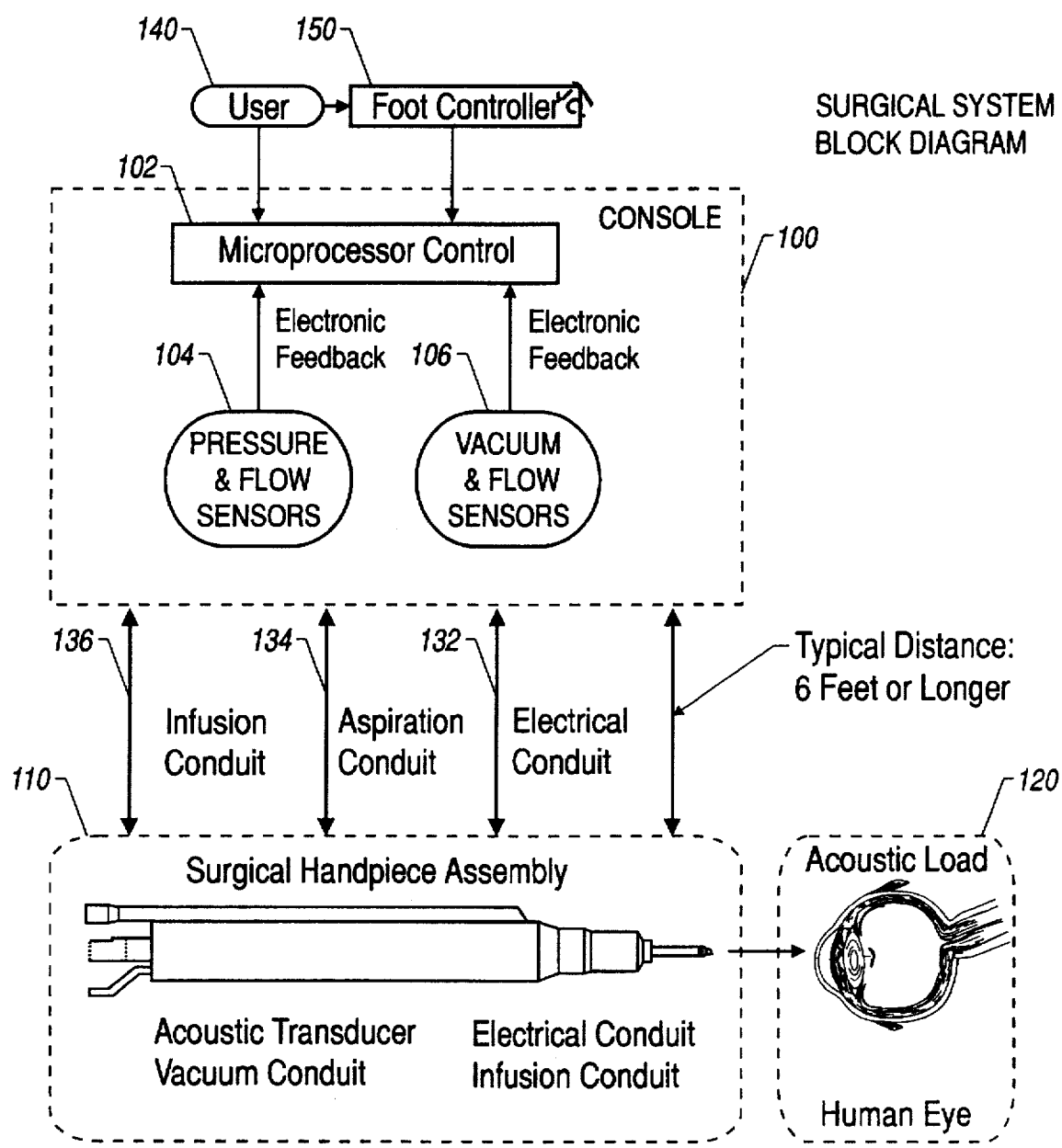
FIG. 1 shows a block diagram of a typical surgical system for phacoemulsification in the prior art.

Fluid transmission paths, e.g. 414, 416, linking the control console 400 with the surgical handpiece 110 via the remote sensor module 420 in FIG. 4, do not have return signal flow arrows pointing into the control console 400 as they do in FIG 1. The significance of this seemingly-subtle difference is important. In the prior art, the sensors 104 and 106 are located within the boundary of the control console 100 of FIG 1. The return arrows indicate the flow of fluid parameter information back into the control console 100. Sensors 104 and 106 interpret that information and convert it into analog electrical signals. Those analog electrical signals are then converted to digital electronic signals, suitable for manipulation by the microprocessor 102. Thus the prior art significantly reduces the speed of information exchange between the control console 100 and surgical handpiece 110 and suffers information loss described above that is inherent and associated with compliant fluid transmission paths.

The present embodiment includes the important improvement in the present invention over the prior art in that the sensors 422 and 424 are deployed in close proximity, e.g inches, with the surgical handpiece 110. This eliminates the return information path by the compliant fluid conduits 414 and 416, and also eliminating the time delays and inherent information loss associated with those compliant fluid transmission paths.

The information transmission path in the present embodiment uses an electrical conduit 412, with significant improvements in transmission speed and major reductions in information loss. The gain in transmission speed of the present invention over the prior art is at least 6 or 7 orders of magnitude as compared with the prior art. For example, it takes tenths of a second in the best prior art systems to transmit information over a typical 6-foot fluid conduit whereas only less than 10 nanoseconds ($1\times10^{-8}$ sec) is needed for electrical/electronic transmission over the same distance. For the comparison to be completely fair, the sensor conversion delay must be included since it must occur before the information can be transmitted via the electrical conduit 412. In that case, add another 100 microseconds ($10^{-4}$ sec) or even a few milliseconds ($10^{-3}$ sec) to the total transmission delay. The improvement in transmission speed is still at least 100 to 1000 times, or 2 to 3 orders of magnitude faster.

Figure 5:
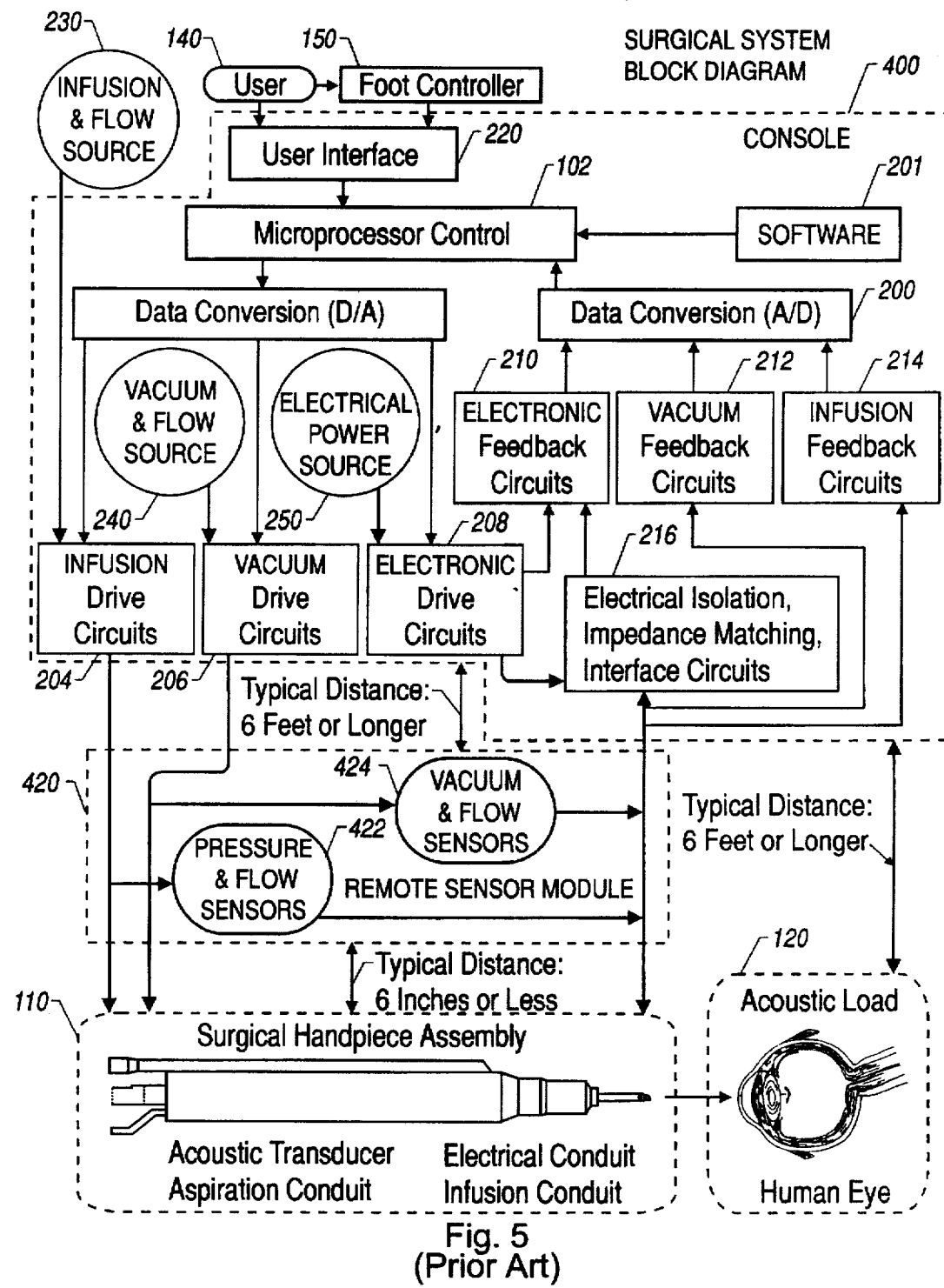
FIG. 5 is a detailed illustration of the first embodiment of the present invention as in FIG. 4 with emphasis on interconnection between the drive circuits (actuators) and the fluid steams for infusion and aspiration.

FIG. 5 shows more detail regarding the system block diagram for the first embodiment. An important difference is in the physical initiation point for the electronic feedback signals for fluid flow and fluid pressure parameter information. The electronic feedback signals for fluid flow and fluid pressure parameters are generated by the sensors 422 and 424 in the remote sensor module 420. The first embodiment shown in FIG. 4 deploys the sensors 422 and 424 at a remote location from the control console 400 that is intermediate in the fluid communication path between the control console 400 and the surgical handpiece 110, and importantly, in closer proximity with the surgical handpiece 110 (typically several inches) than with the control console (typically more than 6 feet).

Figure 3:
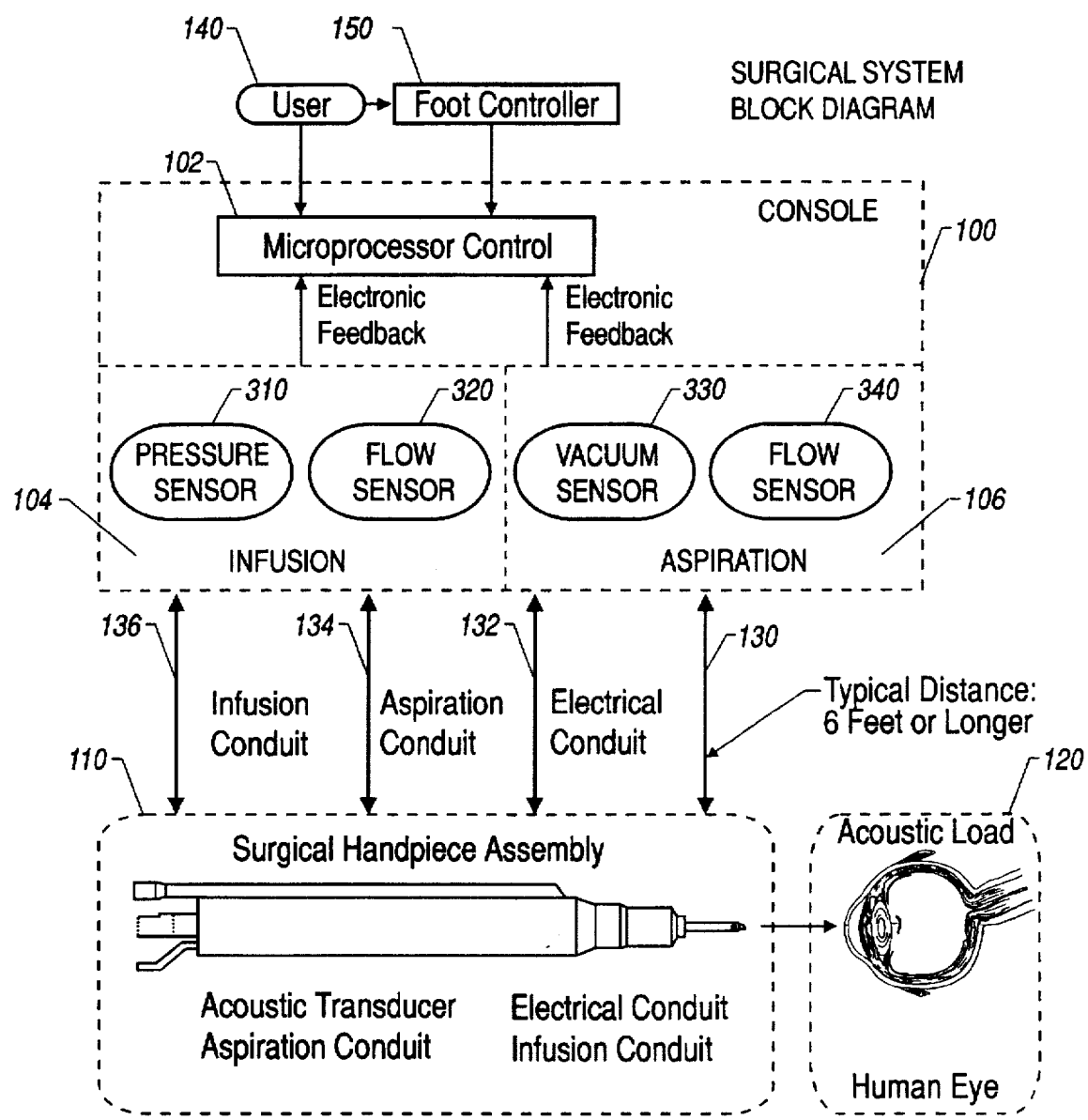
FIG. 3 shows further details on sensor units of a prior art system as in FIG. 1.
Figure 6:
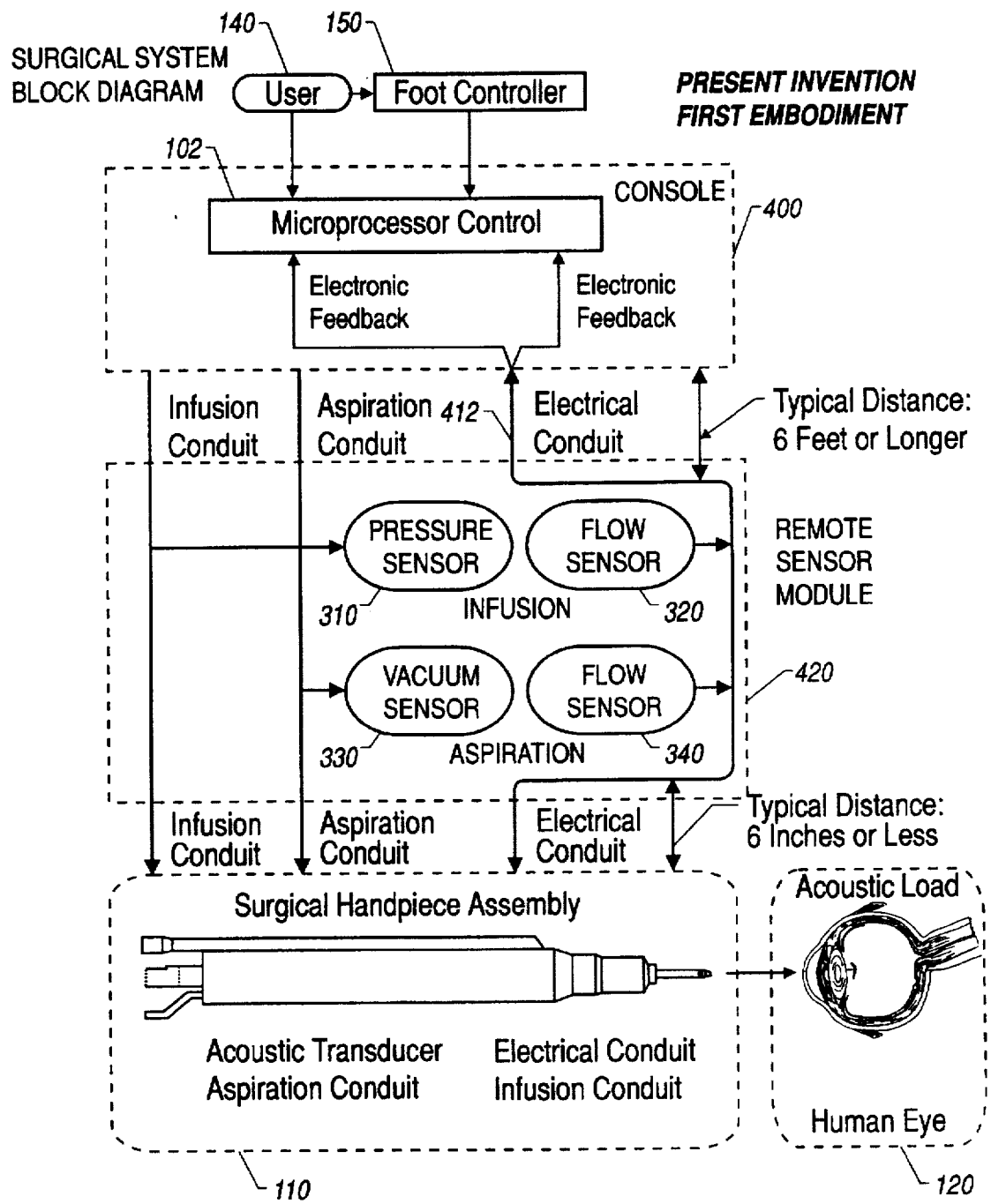
FIG. 6 shows further details on remote sensor units of the first embodiment of the present invention as in FIG. 4.

The earlier discussion on the directional arrows associated with the fluid conduits becomes even more clear in FIG. 5 because the return arrows for fluid parameter information go into the sensors 422 and 424. In the prior art as shown in FIG. 1, analogous sensors 104 and 106 reside within the boundary of the control console 100. In the first embodiment, sensors 422 and 424 are located outside the boundary of the control console 400 at the remote sensor module 420. As shown in FIG. 6 with additional details for the first embodiment, similar to FIG. 3 for the prior art, the individual sensors for fluid flow and pressure are shown within the sensor blocks.

Figure 7:
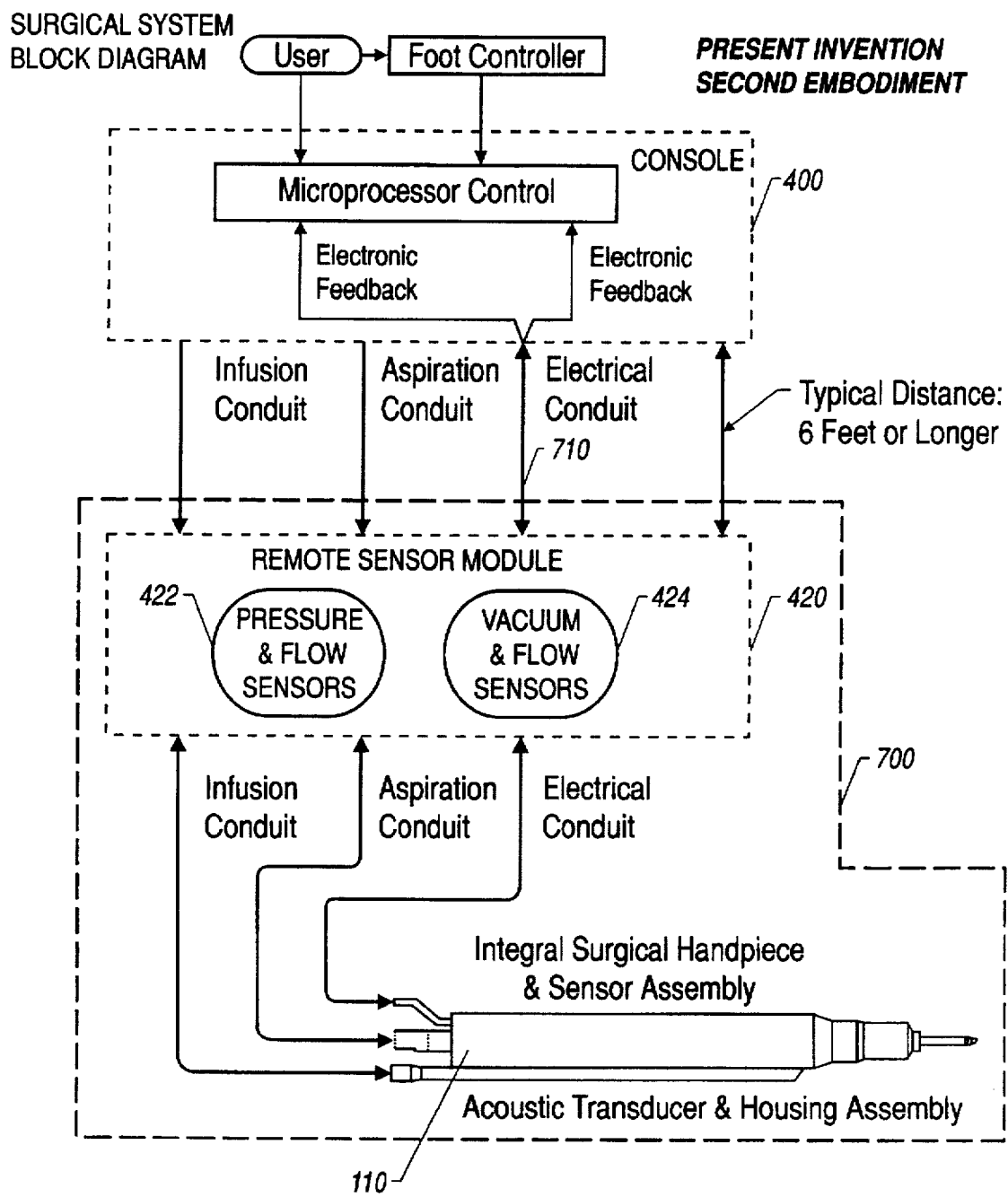
FIG. 7 is a block diagram for the second embodiment of the present invention.

FIG. 7 shows the second embodiment of the present invention. The remote sensor module 420 and the surgical handpiece 110 are integrated together as an integrated surgical handpiece assembly 700. As with the first embodiment, the electrical feedback signals from the fluid flow and pressure sensors 422 and 424 within the remote sensor module 420 are sent through the electrical conduit 710, at rapid electronic transmission speeds.

Figure 2:
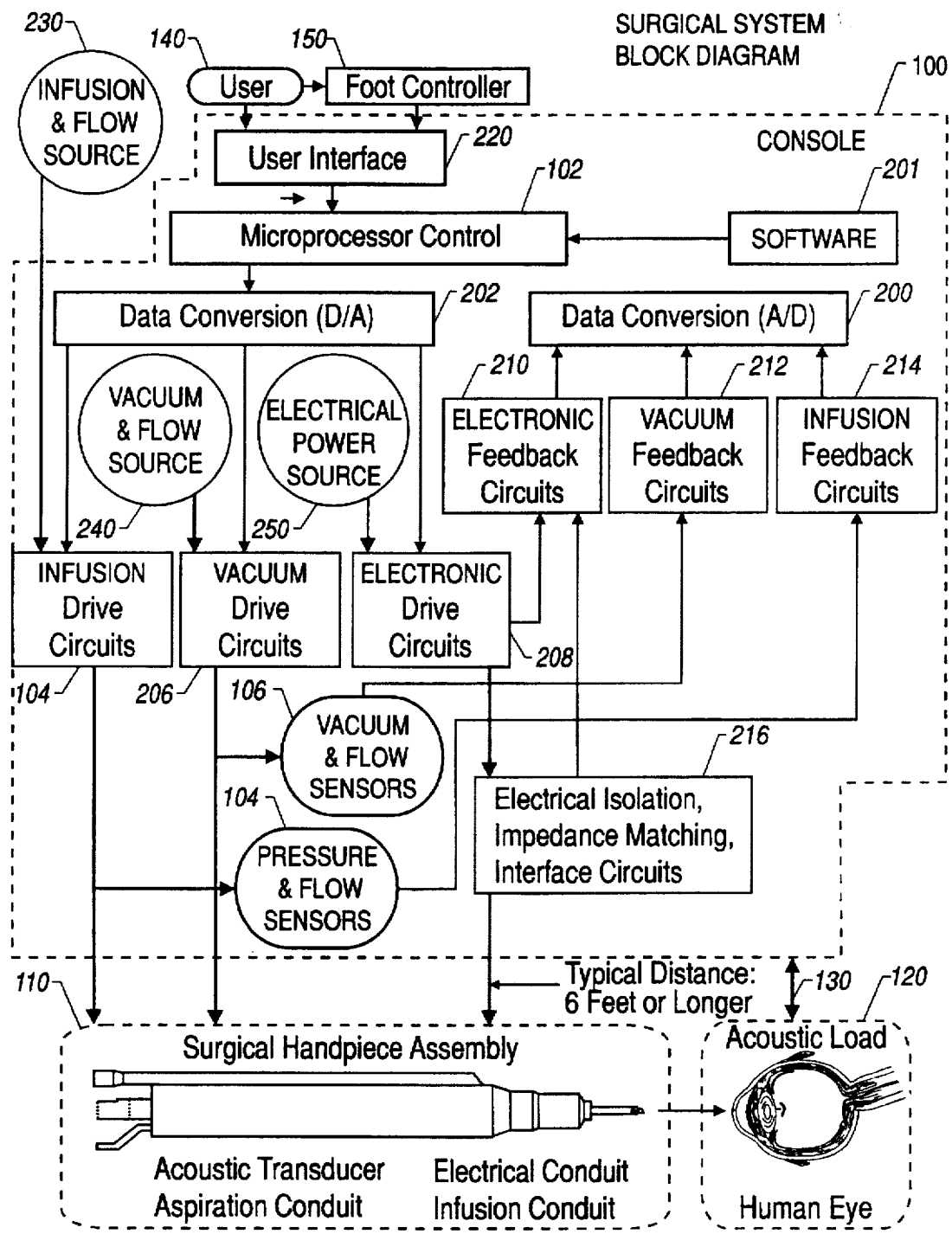
FIG. 2 is detailed illustration of a prior art system as in FIG. 1 with emphasis on interconnection between the drive circuits (actuators) and the fluid steams for infusion and aspiration.
Figure 8:
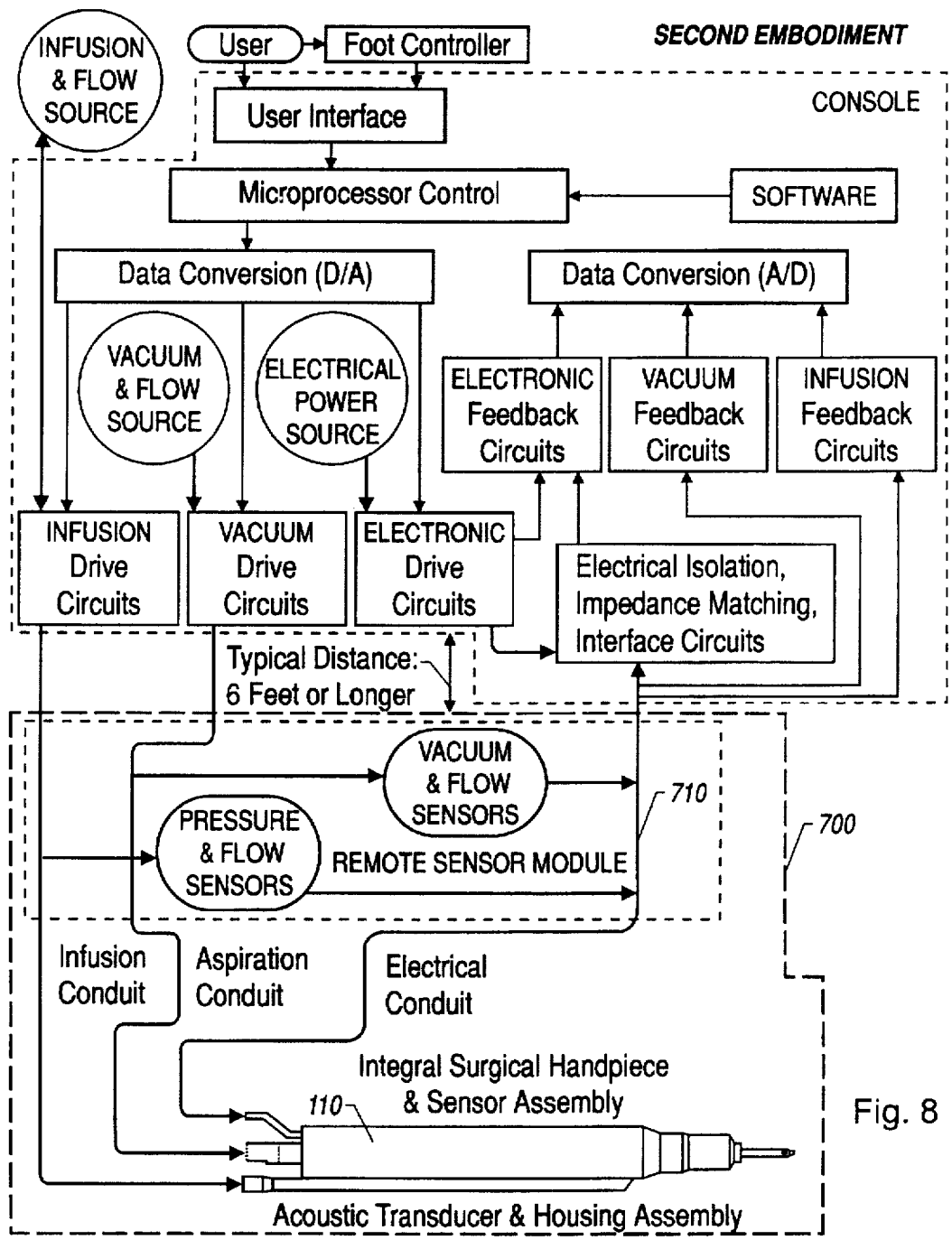
FIG. 8 is a detailed illustration of the second embodiment of the present invention as in FIG. 7 with emphasis on interconnection between the drive circuits (actuators) and the fluid steams for infusion and aspiration.
Figure 9:
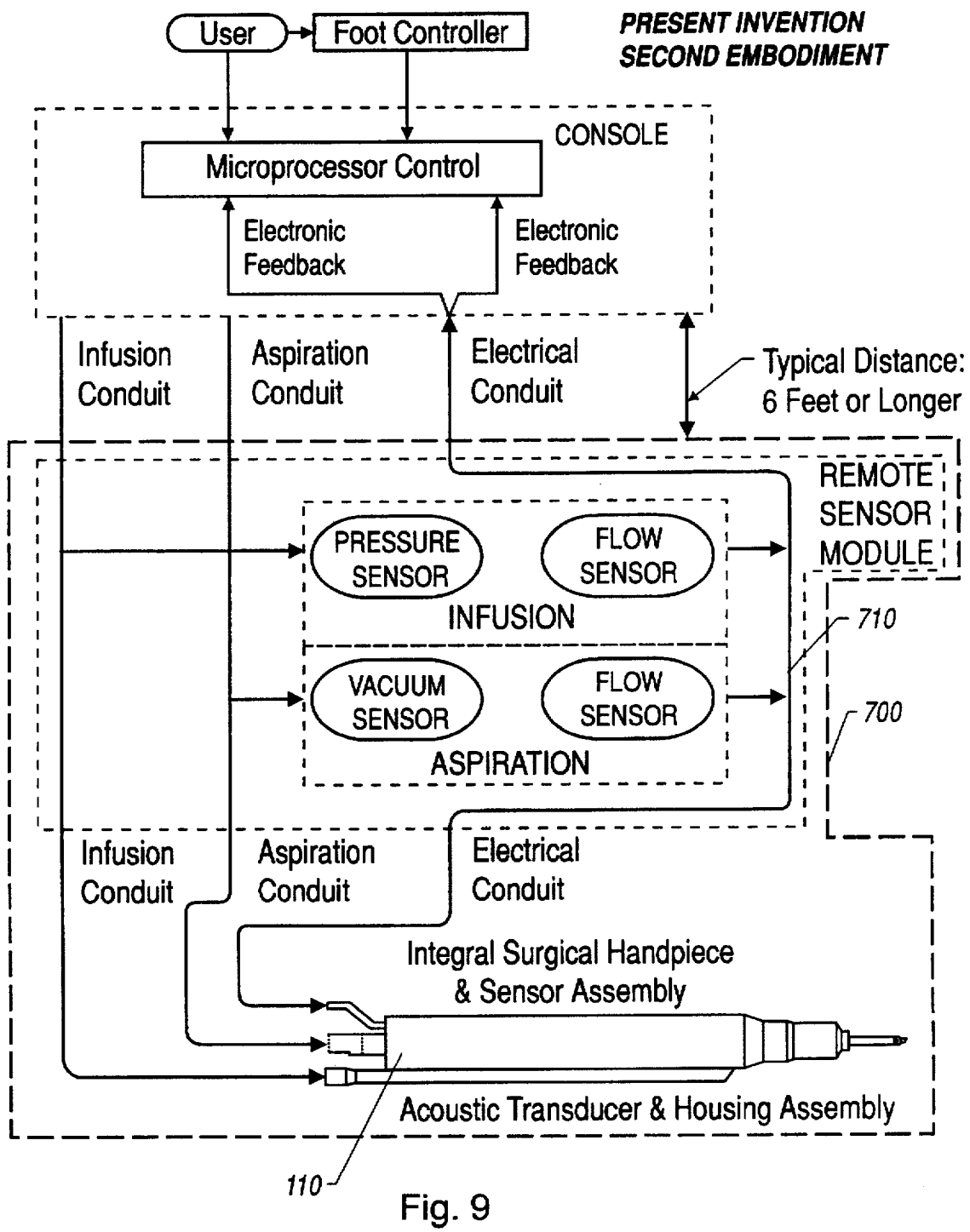
FIG. 9 shows further details on the integrated surgical handpiece including the sensor units of infusion and aspiration for the first embodiment of the present invention as in FIG. 8.

FIG. 8 shows the detail of the system block diagram for the second embodiment, similar to FIG. 5 for the first embodiment and FIG. 2 for the prior art. As shown in FIG. 9, similar to FIG. 6 for the first embodiment and FIG. 3 for the prior art, the individual sensors for fluid flow and pressure are shown within the sensor blocks.

A further advantage is derived in the second embodiment over that of the first embodiment, by deploying the fluid parameter sensors 422 and 424 within the boundary of the integrated surgical handpiece assembly 700. The advantage to the surgeon is a more compact instrument, not encumbered by the additional remote sensor module 420 between the surgical handpiece 110 and the control console 400 as illustrated in FIGS. 4–6.

Compact sensors based on micro electro-mechanical systems (MEMS) can be used to practice the present invention. The preferred MEMS sensor for both the first and second embodiment of the present invention is a circular capacitive pump type sensor. Surface micromachining techniques are used to fabricate MEMS sensors on a silicon wafer. The processed wafer is then cut into small pieces of MEMS sensors, e.g., no more than 2 mm×2 mm for each piece.

Figure 10:
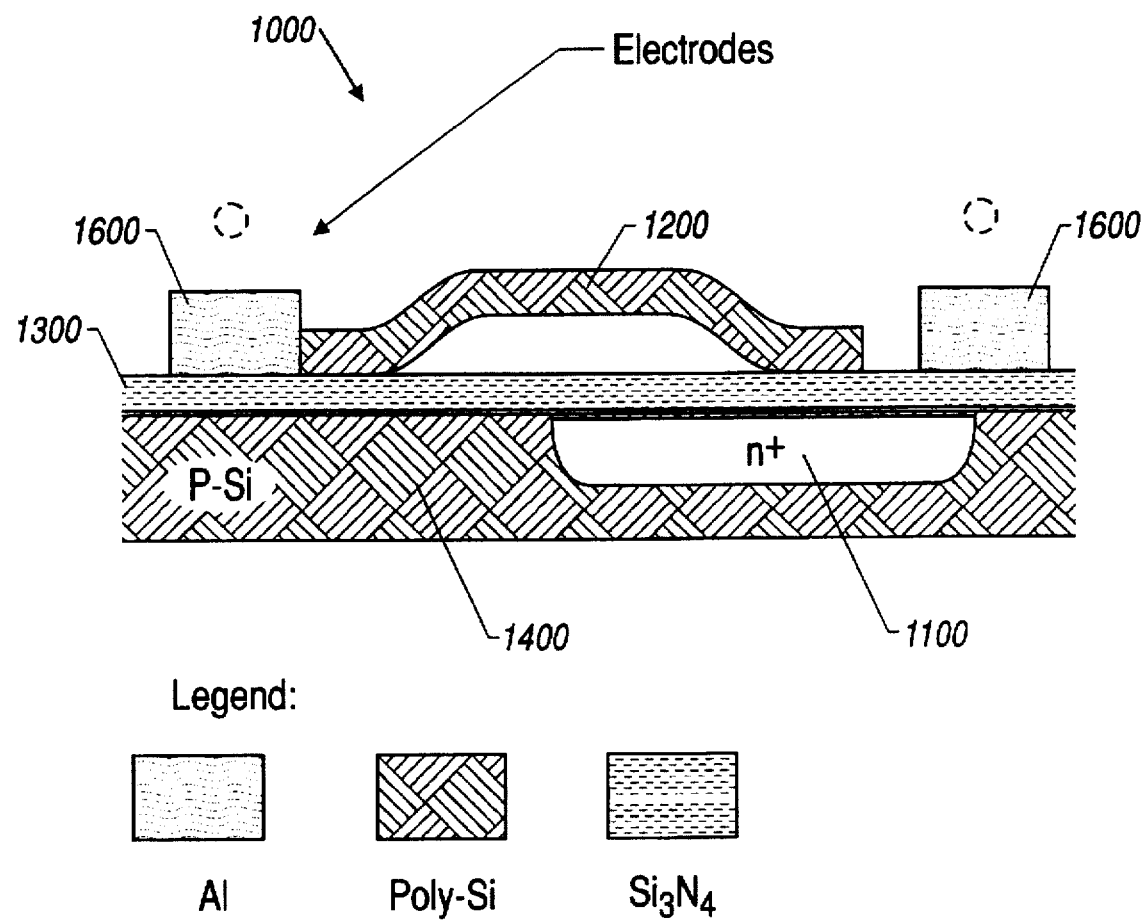
FIG. 10 is a cross sectional view of the compact MEMS sensor device.
Figure 11:
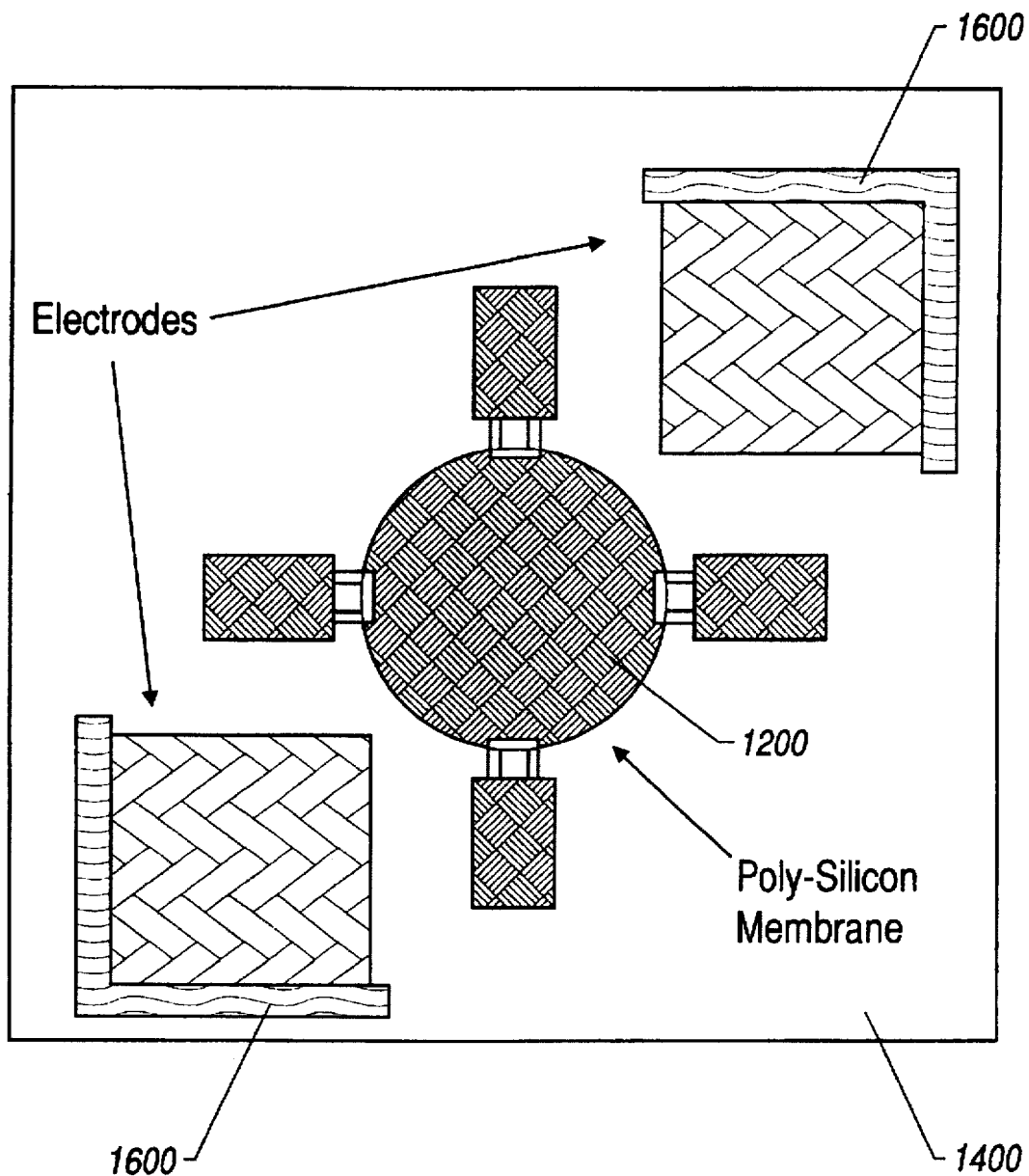
FIG. 11 is a top view of the compact MEMS sensor device.
Figure 12:
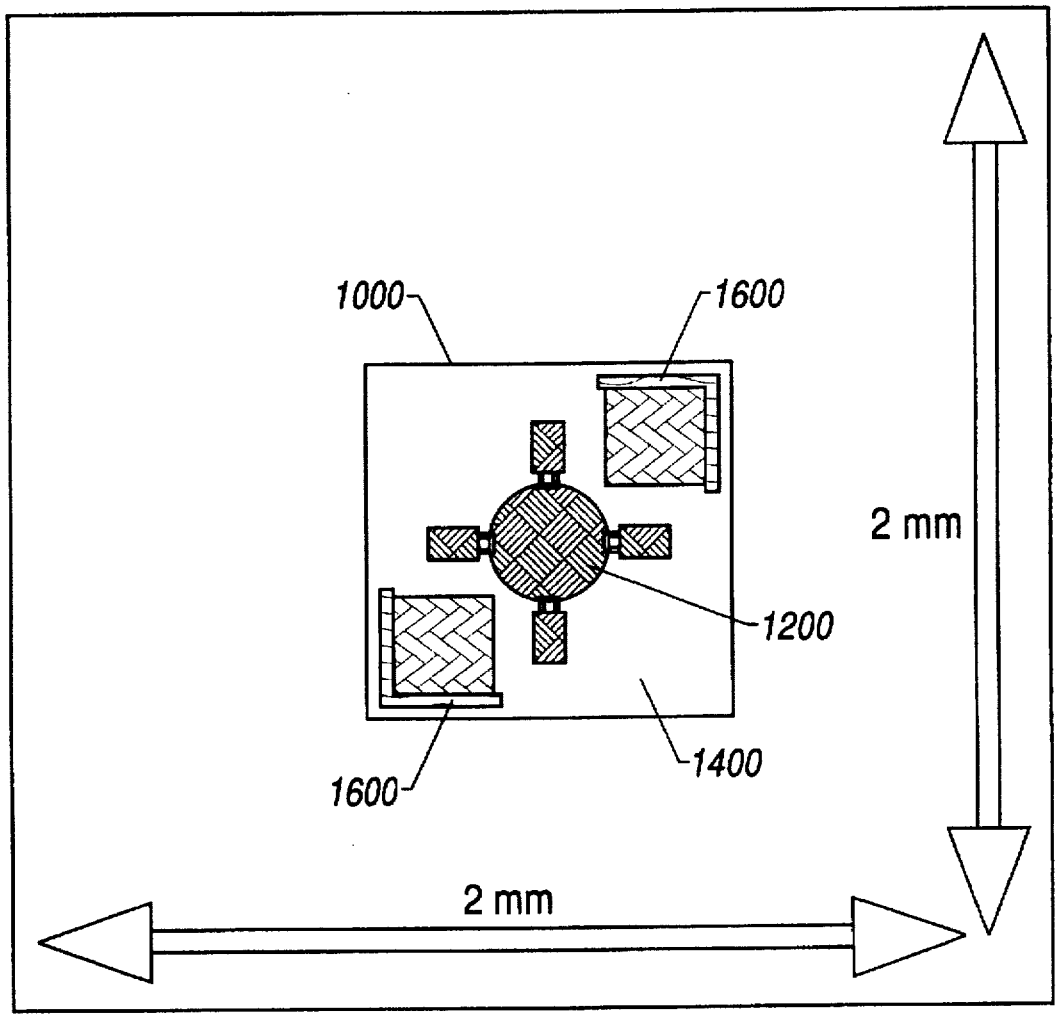
FIG. 12 is a top view of the MEMS sensor device showing dimensions thereof.

FIG. 10 shows the side view of a MEMS capacitive pump sensor 1000. The top membrane 1200 is made of polysilicon. The pressure is detected when the distance between the polysilicon membrane 1200 and the n+ well 1100 changes. The distance change is due to the deformation of the polysilicon membrane 1200. A layer of silicon nitride 1300 is used as an insulator to make sure that the polysilicon membrane 1200 does not create an electrical short circuit with the n+ well 1100. The electrical parameter manifestation of the pressure change, as measured across the electrodes 1600, is a change in the capacitance between the electrode terminals. FIG. 12 shows that the cut out MEMS pressure sensor is less than 1 mm on a side. These dimensions result in a footprint at least 20 times smaller than typical sensors employing prior art technology.

A flow sensor can be constructed by using two MEMS pressure sensors connected in series and measuring the change of pressure over a known length of a fluid transmission conduit of known cross-section area. The laws of fluid dynamics dictate the relationship between a pressure differential over a distance, and the fluid flow in the conduit over that same distance.

As described above, the present invention significantly improves the performance of surgical systems for phacoemulsification in terms of overall system response speed, accuracy in parameter control for infusion and aspiration at the surgical site, system integration, and easy-to-use user interface.

Although the invention has been shown and described with respect to preferred embodiments thereof, it should be understood by those skilled in the art that various modifications and enhancements may be made without departing from the spirit and scope of the present invention that is intended to be encompassed in the following claims, in which:

What is claimed is:

1. A surgery system, comprising:

a surgical handpiece having a housing including at least one aperture interfacing with other modules in said system, a surgical operating element, and an aspiration unit including a first fluid conduit having inner surfaces which allow injection of infusion material, and a second fluid conduit having inner surfaces that allow withdrawal of suction material;

a surgical sensing module, associated with said surgical handpiece and including a pressure sensing device and a flow sensing device, fluid interfacing units connecting to said surgical handpiece, and electrical interfacing units connecting with other modules in said system, said surgical sensing module operating to monitor fluid pressure and fluid flow parameters in said surgical operating element in said surgical handpiece; and a system control module, having a housing including at least one aperture interfacing with other modules in said system, an electronic information processing device, electrical interfacing units connecting said system control module with said surgical sensing module and said surgical handpiece, and a user interface including an input device and an output device, said system control module operating to receive information indicative of said pressure and flow parameters from said surgical sensing module and to control said surgical operating element, fluid infusion and suction in said surgical handpiece.

2. A system as in claim 1, wherein said surgical sensing module is disposed to deploy said pressure sensing device and said flow sensing device physically inside said housing for said surgical handpiece.

3. A system as in claim 1, wherein said surgical sensing module is disposed physically outside of said housing for said surgical handpiece with a distance less than eight inches from said surgical handpiece.

4. A system as in claim 1, wherein said surgical operating element in said surgical handpiece has a phacoemulsification device, said phacoemulsification device having an electrical conduit connecting to said system control module to provide communication therebetween.

5. A system as in claim 3, wherein said phacoemulsification device has a ultrasonic transducer.

6. A system as in claim 1, further including:
 a fluid source disposed to connect with said system control module and said surgical hand piece, operating to provide said infusion material to said surgical handpiece; and
 a vacuum source disposed to connect with said system control module and said surgical hand piece, operating to perform said suction.

7. A system as in claim 6, wherein said system control module further controls said fluid source and said vacuum source to maintain said fluid pressure and fluid flow at predetermined values in said surgical operating element in said surgical handpiece.

8. A system as in claim 1, wherein said electronic information processing device is a microprocessor.

9. A method for integrating a phacoemulsification surgical system, comprising:

integrating a phacoemulsification device in a surgical handpiece, said surgical handpiece having electrical conduits for transferring electrical power to said phacoemulsification device and communication and fluid conduits for infusion and suction;

providing a surgical sensing module for said surgical handpiece including a pressure sensing device and a flow sensing device, fluid interfacing units connecting to said fluid conduits in said surgical handpiece and other fluid units in said system, and electrical interface units connecting with other modules in said system, said surgical sensing module operating to monitor fluid pressure and fluid flow parameters in said phacoemulsification device in said surgical handpiece;

providing a system control module to said surgical system, said system control module having a housing including at least one aperture interfacing with other modules in said system, an electronic information processing device, electrical interface units connecting said system control module with said surgical sensing module and said surgical handpiece, and a user interface including an input device and an output device, said system control module operating to receive information indicative of said pressure and flow parameters from said surgical sensing module and to control said surgical operating element, fluid infusion and suction in said surgical handpiece;

interconnecting said surgical handpiece and said system control module interconnect with each other only by said electrical conduits; and deploying said surgical sensing module relative to said phacoemulsification device at a distance of less than 8 inches.

* * * * *